United States Patent [19]

Polk, Jr. et al.

[11] Patent Number: 5,198,212
[45] Date of Patent: Mar. 30, 1993

[54] METHOD AND COMPOSITIONS FOR TREATMENT OF TRAUMA-ASSOCIATED SEPSIS WITH GAMMA INTERFERON

[75] Inventors: Hiram C. Polk, Jr., Louisville, Ky.; Gerald Sonnenfeld, Pittsburgh, Pa.; Christopher D. George, Earlsfield London, Great Britain

[73] Assignee: University of Lousville Research Foundation Incorporated

[21] Appl. No.: 730,017

[22] Filed: Jul. 12, 1991

Related U.S. Application Data

[63] Continuation of Ser. No. 265,411, Oct. 31, 1988, abandoned.

[51] Int. Cl.$^5$ ............................................. A61K 37/66
[52] U.S. Cl. .................................................... 424/85.5
[58] Field of Search ........................................ 424/85.5

[56] References Cited

U.S. PATENT DOCUMENTS

| | | |
|---|---|---|
| 4,480,032 | 10/1984 | Yabrov ............................... 424/85.7 |
| 4,762,791 | 8/1988 | Goeddel et al. . |
| 4,879,111 | 11/1989 | Chong . |

FOREIGN PATENT DOCUMENTS

| | | |
|---|---|---|
| 0077670 | 4/1983 | European Pat. Off. . |
| 0146354 | 6/1985 | European Pat. Off. . |
| 0217645 | 4/1987 | European Pat. Off. . |
| 0242233 | 10/1987 | European Pat. Off. . |
| 0254593 | 1/1988 | European Pat. Off. . |
| 0257956 | 2/1988 | European Pat. Off. . |

OTHER PUBLICATIONS

Chemical Abstracts, vol. 109, Abstract No. 53109, 1988.
Chemical Abstracts, vol. 109, Abstract No. 52921g, 1988.
Chemical Abstracts, vol. 109, Abstract No. 21362d, 1988.
Chemical Abstracts, vol. 109, Abstract No. 14770f, 1988.
Alexander et al., *Surgical Infectious Diseases*, Chapter 17, Howard et al., eds., Appleton & Lange, Norwalk, Conn. (1988).
Allgower et al., *Surg. Clin. N. Am.*, 60, 133–144 (1980).
Baker et al., *J. Trauma*, 14, 187–196 (1984).
Baron et al., *Antiviral Res.*, Suppl. 1, 173–183 (1985).
Billiau, *Nature*, 331, 665 (1988).
Black et al., *J. Immunol.*, 138, 491–495 (1987).
Blanchard et al., *J. Immunol.*, 136, 963–970 (1986).
Brook, *Radiation Research*, 115, 1–25 (1988).
Bukholm et al., *Infection and Immunity*, 42, 1198–1202 (1983).
Bukholm et al., *Infection and Immunity*, 45, 62–66 (1984).
Bukholm et al., *J. Interferon Res.*, 7, 409–417 (1987).
Burges et al., *Arch. Dermatol.*, 123, 1346–1350 (1987).
Campbell et al., *Can J. Microbiol.*, 21, 1247–1253 (1975).
Cushing, *Surg. Clin. N. Am.*, 57, 165–177 (1977).
Fry et al., *Trauma: Clinical Care and Pathophysiology*, Ch. 4, Year Book Medical Publishers, Inc. Chicago, Ill. Richardson et al., ed. p. 41 (1986).
Ghadirian et al., *Immunobiology*, 176, 341–353 (1988).
Heremans et al., *J. Immunology*, 138(12), 4175–4179 (1987).
Hershman et al., *Clin. Exp. Immunol.*, 72, 406–409 (1988).
Hershman et al., *Infection and Immunity*, 56(9), 2412–2416 (1988).
Hershman et al., *Injury*, 19, 263–266 (1988).
Hershman et al., *J. Interferon Res.*, 7, 815, Abstract III-39 (1987).
Hershman et al., *J. Interferon Res.*, 8, 367–373 (1988).
Hershman et al., *J. Interferon Res.*, 7, 695 (1987) presented in part at the annula meeting of the International Society for Interferon Research on the Interferon System, Washington, D.C., Nov. 2–6, 1987.

(List continued on next page.)

*Primary Examiner*—Merrell C. Cashion, Jr.
*Assistant Examiner*—Choon Koh
*Attorney, Agent, or Firm*—Marshall, O'Toole, Gerstein, Murray & Bicknell

[57] ABSTRACT

Trauma-associated sepsis is effectively treated using gamma interferon alone or in combination with an antibiotic.

17 Claims, 7 Drawing Sheets

OTHER PUBLICATIONS

Hershman et al., *Microbial Pathogenesis*, 4, 165–168 (1988).
Izadkhah et al., *J. Interferon Res.*, 1, 137–145 (1980).
Karam et al., *Arch. Intern. Med.*, 143, 2073–2074 (1983).
Kaufman et al., *Eur. J. Immunol.*, 17, 237–246 (1987).
Livingston and Malagoni, A Presentation made at The First International Congress on the Immune Consequences of Sepsis and Shock, Munich, West Germany, Mar. 3–5, 1988.
Livingston and Malangoni, A Presentation on the Effect of IFN-$\gamma$ on Infection Following Hemorrhagic Shock at the 66th Annual Meeting of the American College of Surgeons, Committee in Trauma, Feb. 25, 1988.
Livingston et al., *Arch. Surg.*, 123, 1309–1312 (1988).
Livingston et al., *J. Surg. Res.*, 45, 37–43 (1988).
Livingston et al., "Tumor Necrosis Factor-Alpha (TNF-$\alpha$) Decreases Infection after Hemorrhagic Shock," in part at the Sep., 1988 Metting of the Trauma Society.
Maluish et al., *J. Clin. Oncol.*, 6, 434–445 (1988).
Murphy et al., *Annals of Internal Medicine*, 108, 36–41 (1988).
Murray, *Annals of Internal Medicine*, 108, 595–608 (1988).
Murray et al., *J. Immunol.*, 134, 1619–1622 (1983).
Murray et al., *New Eng. J. Med.*, 310, 883–889 (1984).
Nathan et al., *J. Exp. Med.*, 158, 670–689 (1983).
Niesel et al., *Infection and Immunity*, 52, 828–833 (1986).
Pfefferkorn et al., *Infection and Immunity*, 44, 211–216 (1984).
Polk et al., *Surgery*, 90, 376–380 (1981).
Polk et al., *Ann. Surg.*, 204, 282–299 (1986).
Rubin et al., *Proc. Nat'l Acad. Sci. (USA)*, 77(10), 5928–5932 (1980).
Solovev et al., "Method for Treating Acute Respiratory Viral Infections in Newborns with Purulent-Septic Diseases," Order of the Red Banner of Labor Scientific Research, Institute of Epidemiology, Microbiology and Hygiene, Moscow, U.S.S.R., Bulletin No. 6 (1986) (Trans. from the Russian.
Spillert et al., *The American Surgeon*, 50, 653–655 (1984).
Subbarao et al., *AJDC*, 141, 1018–1020 (1987).
Weigent et al., *Infection and Immunity*, 49, 593–597 (1985).
Wong et al., *Nature*, 323, 819–822 (1986).
Zoon et al., *Pharmac., Ther.*, 24, 259–278 (1984).
Zueva et al., *UDC*, "Inhibition of Staphylococcal Infection with Interferon," (Translated from the Russian).

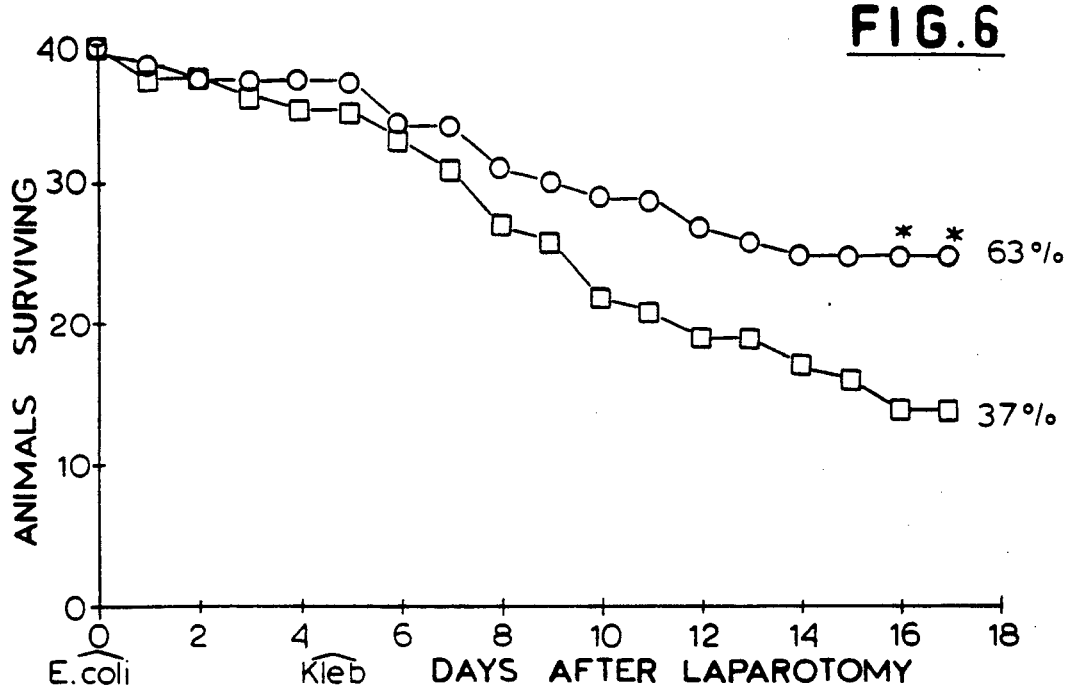
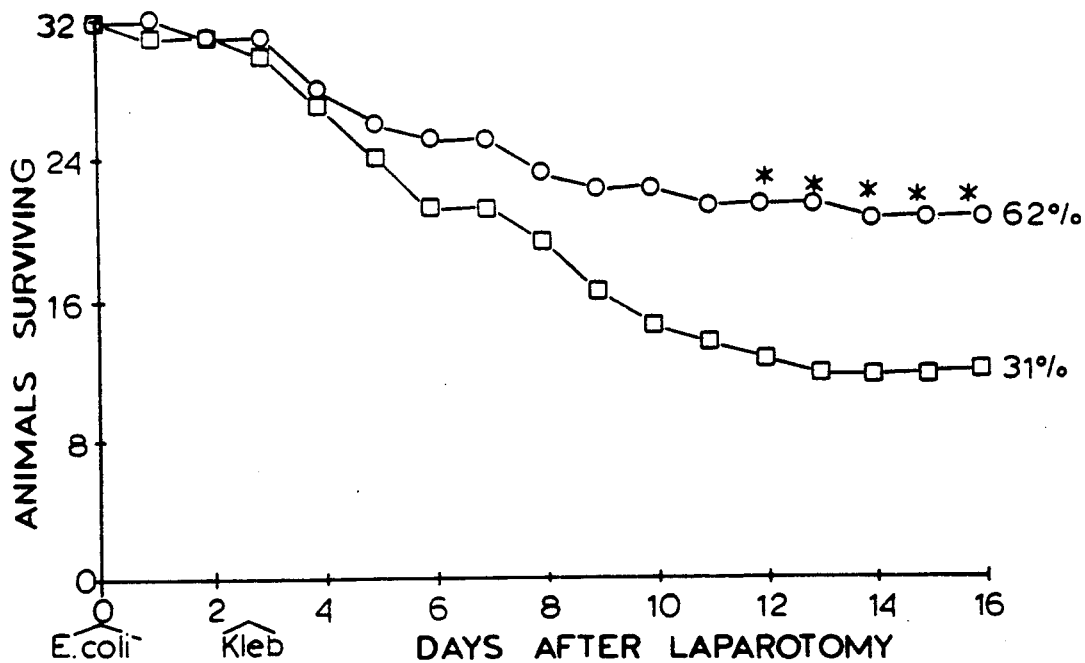

METHOD AND COMPOSITIONS FOR TREATMENT OF TRAUMA-ASSOCIATED SEPSIS WITH GAMMA INTERFERON

This application is a continuation of application Ser. No. 07/265,411, filed Oct. 31, 1988, now abandoned.

BACKGROUND

The present invention relates in general to methods and compositions for treatment of trauma-associated sepsis, and in particular to methods and compositions including gamma interferon ("IFN-Y$_\gamma$"), especially human IFN-$_{65}$, for treatment of traumaassociated sepsis.

Infection remains the major cause of late death in trauma patients. Antibiotics, sterile techniques, mechanical barriers, and conventional treatment have met with limited success in preventing or controlling these infections.

A number of immunological parameters have been shown to be depressed after trauma. Expression of HLA-DR antigen (which corresponds to the Ia antigen in mouse models) is decreased on monocytes of human trauma patients.

Viral infections and tumors may be treated using $\alpha$-interferon or IFN-$\gamma$ as may intracellular bacterial infections. In a suggested mechanism for the effect of IFN-$\gamma$ on intracellular bacterial infections, it is proposed that the IFN-$\gamma$ prevents uptake of the bacteria by cells. This mechanism does not relate to infections which are not intracellular in nature.

SUMMARY OF THE INVENTION

A method according to the present invention for treatment of trauma-associated sepsis, particularly of a bacterial blood infection caused by an enteric bacterium, includes the step of administering a therapeutically effective dose of IFN-$\gamma$ to a victim of trauma, and in particular, to a trauma patient not known to have a viral infection, a tumor or an intracellular bacterial infection. The method involves introducing IFN-$\gamma$ into a bodily fluid of a patient. This introduction may be effected by injecting IFN-$\gamma$ subcutaneously, intramuscularly or intravenously. Intravenous administration may be by infusion or bolus injection. The IFN-$\gamma$ used according to the present invention is preferably desCys-TyrCys human IFN-$\gamma$.

A method according to the present invention preferably also involves co-administering an antibiotic with the IFN-$\gamma$. Co-administration may be effected by administration of the antibiotic and IFN-$\gamma$ during the course of the same infection, or may be effected by inclusion of the antibiotic and IFN-$\gamma$ in the same composition (particularly where administration is by intravenous infusion).

The antibiotic may be selected from the group consisting of cefazolin, nafcillin, vancomycin, cefoxitin, neomycin plus erythromycin, penicillin G, trimethoprim plus sulfamethoxazole, and clindamycin or clindamycin plus gentamycin or tobramycin.

A composition for treatment of trauma-associated sepsis according to the present invention includes IFN-$\gamma$, an antibiotic and a diluent or carrier. The antibiotic may be selected from the group consisting of cefazolin, nafcillin, vancomycin, cefoxitin, neomycin plus erythromycin, penicillin G, trimethoprim plus sulfamethoxazole, and clindamycin or clindamycin plus gentamycin or tobramycin.

BRIEF DESCRIPTION OF DRAWINGS

FIG. 6 is a graphic depiction of the effect of administration of IFN-$\gamma$ according to the present invention on survival of mice after laparotomy when a second bacterial challenge was administered five days after a first challenge;

FIG. 7 is a graphic depiction of the effect of administration of IFN-$\gamma$ according to the present invention on survival of mice after laparotomy when a second bacterial challenge was administered three days after the first challenge;

DETAILED DESCRIPTION

Figure 1:
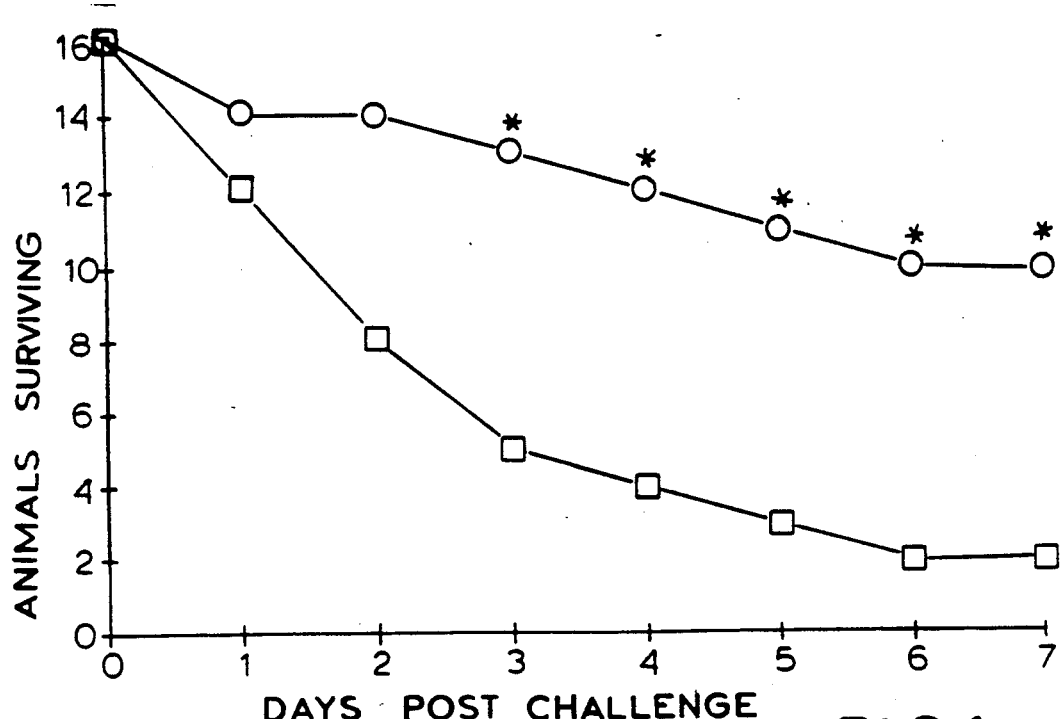
FIG. 1 is a graphic depiction of the improvement in survival after IFN-$\gamma$ treatment according to the present invention in a suture-challenge model.

Trauma-associated sepsis or infection remains a serious problem despite advances in antibacterial chemotherapy. According to the present invention, augmenting host immune defenses with IFN-$\gamma$ increases the frequency of survival of patients suffering from such sepsis or infection.

Trauma-associated sepsis is defined herein as the presence of extracellular bacteria in the blood or tissues ("sepsis") associated with a wound or injury. Bacteria characteristic of trauma-associated sepsis include enteric bacteria, and in particular include coliform bacteria, bacilli of the genus Klebsiella and bacilli of the genus Pseudomonas. Trauma includes physical injury such as surgical incision.

Bacteria which are recognized as being associated with trauma include: Gram-positive bacteria such as *Staphylococcus aureus, Streptococcus faecalis*, Pneumococci, anhaemolytic Enterococci, Sarcina species and haemolytic Streptococci; and Gram-negative bacteria such as Escherichia coli, Pseudomonas species, *Klebsiella* species, *Proteus* species, *Enterobacter cloacae*, coliform bacteria, *Serratia* species, *Citrobacter* species and *Providencia* species [Allgower et al., *Surg. Clin. N. Am.*, 60, 133–144 (1980)].

Thus, trauma-associated sepsis may be distinguished from other forms of bacterial infection as being characterized by the presence of trauma (i.e., injury, such as a burn or a wound) and the relative predominance of bacteria which are not intracellular in location. Sepsis after trauma usually occurs within two weeks after injury in patients who are immunosuppressed as a result of the trauma. Sepsis may be due to microbial contamination at the time of trauma, or to spillover of organisms from the gut.

Human IFN-γ is defined herein as a polypeptide having the sequence of native gamma interferon as set forth in European Publication No. 77,670 and all amino acid sequence or other variants thereof which are capable of activation of monocytes from trauma patients. Examples of such variants are alleles or the products of site directed mutagenesis in which residues are deleted, inserted or substituted. For example, see European Publication No. 146,354.

IFN-γ according to the present invention may be derived from any source, including IFN-γ isolated from natural sources, and chemically synthesized or recombinantly-produced IFN-γ.

IFN-γ should be used which is homologous to the animal species to be treated since it may not be active across species lines. In human therapy, the desCysTyrCys variant of the sequence shown in EP 77,670 is preferably employed, and optionally the C-terminal variant in which the last 4 residues are deleted in post-translational processing. IFN-γ having native sequences is obtained by purification from natural sources using known methods. The same molecule or its variants are obtained from recombinant sources, also by known methods.

A typical formulation may contain IFN-γ (20 X 10$^6$ U) at 1.0 or 0.2 mg/ml, succinic acid at 0.27 mg/ml, disodium succinate hexahydrate 0.73 ml/injection at pH 5.0. This aqueous formulation is administered at therapeutic doses, which are less than the maximum tolerated dose in humans as determined by the clinician. IFN-γ may also suitably administered from a reconstituted lyophilized preparation.

IFN-γ may be administered by any conventional route that directs a therapeutic dose to the site of the trauma, for example, by intravenous or intrapulmonary (European Publication No. 257,956) delivery routes. Administration may be by continuous infusion or bolus dosing in sufficient amounts to maintain therapeutic levels. IFN-γ may be administered prior to the trauma, in the case of surgical trauma, or as soon as possible following accidental or non-surgical trauma, and then continued for a time sufficient to permit proper healing of the trauma, typically about from 3 to 14 days or such other period as is determined by the clinician.

IFN-γ is preferably administered according to the present invention subcutaneously at doses of from 0.01 to 0.1 mg/m$^2$/day for 7–10 days. However, other routes of administration, such as intramuscular or intravenous administration, may be employed. Moreover, immunologically effective dosage levels may generally be determined for a particular application according to the procedure of Maluish et al., *J. Clin. Oncol.*, 6, 434–445 (1988).

According to the present invention, IFN-γ may be administered therapeutically (i.e. after appearance of sepsis) or prophylactically (i.e., prior to appearance of sepsis).

IFN-γ antibiotics may be co-administered with synergistic effect according to the present invention. Thus, trauma-associated sepsis which is not effectively treated by antibiotics alone may be treated according to the present invention. Antibiotics which may be useful according to the present invention include penicillin, ampicillin, amoxacillin, methicillin, oxacillin, cloxacillin, diclosacillin, nafcillin, carbenicillin, cephalothin, cefazolin, cephradine, cephalexin, erythromycin, lincomycin, clindamycin, chloramphenicol, tetracycline, doxycycline, minocycline, gentamicin, kanamycin, tobramycin, vancomycin, trimethoprim and sulfamethoxazole. [Cushing, *Surg. Clin. N. Am.*, 57, 165–177 (1977)]

The following Examples more particularly illustrate the invention.

In Example 1, the ability of IFN-γ treatment to alter the course of infection is demonstrated in a model of surgical wound infection. This model simulates a classical surgical wound infection involving pathogenic bacteria, a foreign body, tissue injury and an open wound. Simulation is obtained by placing a suture impregnated with *Klebsiella pneumoniae* ("*K. pneumoniae*") into the thigh of a mouse. Mortality rates are high for untreated animals in this model.

In Example 2, the simulated wound infection-treatment model involves subcutaneous injection of IFN-γ. Bacterial challenge in this model consists of intramuscular injection of *K. pneumoniae.*

In Example 3, an infected burn wound model was used to study the efficacy of IFN-γ therapy. Two different Gram-negative wound infections, specifically those involving *K. pneumoniae* and *Pseudomonas aeruginosa* ("*P. aeruginosa*"), were studied.

Example 4 includes a description of a laparotomy model of clinical conditions following trauma. Bacterial challenge involved intraperitoneal injections of *Escherichia coli* ("*E. coli*") or intramuscular injection of *K. pneumoniae.*

Example 6 is a description of a determination of values for MO$_2$DR (i.e. for monocyte HLA-DR antigen expression) in cultures of blood samples from normal subjects and trauma patients before and after incubation with IFN-γ.

Example 5 involves a description of a study of the effect of IFN-γ on monocyte HLA-DR antigen expression in trauma patients.

HLA-DR antigen expression by monocytes and macrophages is necessary for effective antigen presentation to lymphocytes. Traumatic injury and sepsis reduce HLA-DR antigen expression of monocytes.

In Example 7, a study is described in which patients with severe injury received recombinant IFN-γ therapy along with prophylactic antibiotic therapy.

Example 8 illustrates the increased effectiveness against bacterial infection observed with the use of an antibiotic plus IFN-γ, as opposed to the use of either alone.

EXAMPLE 1

Adult male CBA/J mice, weighing 20–25 g each, (Jackson Laboratories, Bar Harbor, Maine) were deprived of food but allowed free access to water for 24 hours prior to bacterial challenge and refed 4 hours following that challenge. This model has been shown to parallel infections of surgical wounds. Polk et al., *Surgery*, 90, 376 (1981).

Lengths of 3-0 twisted cotton suture were incubated overnight in trypticase soy broth (BBL Microbiological Systems, Cockeysville, Maryland) and inoculated with *K. pneumoniae* (Capsular Type 2). Lengths of suture attached to a French eye needle were inserted aseptically into the right thigh of each mouse and the suture was cut flush with the skin at either end and buried subcutaneously.

Murine IFN-γ, produced by recombinant DNA technology, was a gift of Genentech, Inc., South San Francisco, Calif. The IFN-γ had specific activity of approximately $2.3 \times 10^7$ U/mg protein and was diluted with RPMI-1640 medium (Gibco Laboratories, Grand Island, N.Y.). The interferon was titered prior to use by means of a microplaque reduction assay using the Indiana strain of vesicular stomatitis virus on L-929 cells. Campbell et al., *Can. J. Microbiol.*, 21, 1247–1253 (1975). In this assay, one interferon unit was equivalent to 0.88 NIH G-002-904-511 reference standard units.

IFN-γ was administered subcutaneously into the left or opposite hind limb in daily 0.1 ml injections of 7500 units each. Treatment commenced 5 days prior to suture challenge and the last dose was administered 1 hour prior to this challenge. In all experiments, control animals received 0.1 ml of RPMI-1640 medium subcutaneously at the same time that IFN-γ was administered.

A first experiment assessed the effect of IFN-γ on Survival following suture challenge. Survival of an IFN-γ group (n=16) was compared to a control group (n=16). Surviving mice were observed for a minimum of 3 weeks after bacterial challenge to assess late mortality.

A second experiment determined the effect of IFN-γ on local and systemic bacterial recovery following suture challenge. An IFN-γ group (n=26) was compared to a control group (n=35). Six to eight animals from each group were sacrificed by cervical dislocation at 1, 2 and 3 days after suture challenge. Blood was withdrawn immediately from each sacrificed animal by cardiac puncture. The medial compartment musculature, including the inserted suture, was excised "en bloc" and the suture separated and its length measured with a micrometer. Blood and muscle then underwent quantitative bacteriology. The number of mice that died during the experiment was recorded.

To estimate the initial bacterial inoculum, the number of bacteria per millimeter of suture was determined by homogenizing a 1 cm length of the suture with 10 ml of sterile phosphate buffer saline (PBS), using a glass mortar and electrically-driven Teflon ® pestle. After agitation for 5 minutes, the homogenate was serially diluted in PBS, plated on nutrient agar (BBL Microbiology Systems; Cockeysville, Md.), and incubated overnight at 37° C., after which the bacterial colonies were counted. The number of bacteria initially introduced into an animal was equal to the suture length in millimeters multiplied by the number of bacteria per millimeter in the suture.

Quantitative determination of wound bacteriology was performed in a similar manner. Each excised specimen of muscle, together with the inoculating suture, was homogenized and plated as above. Values for bacterial quantity were determined as $\log_{10}$ of blood bacterial counts or $\log_{10}\%$ local bacterial recovery from muscle. Of the blood removed by cardiac puncture, 0.1 ml was serially diluted with PBS and plated on nutrient agar. After overnight incubation, the number of colony-forming units was counted.

The Student's t Test for independent means was used to analyze muscle and blood culture results, and the Chi Square test with Yates' correction for continuity was used in the analysis of survival data. In all cases, differences were considered significant at $p<0.05$.

The intramuscular dose of Klebsiella introduced with the suture ranged between 1.5 and $2.2 \times 10^6$ organisms. The IFN-γ treated group had significantly greater survival than the control group from day 3 onwards as is illustrated in FIG. 1. In FIG. 1 the survival of mice treated for 5 days prior to suture challenge is plotted using squares to indicate treatment with RPMI-1640 medium (controls) or using circles to indicate treatment with IFN-γ. There were no further deaths after day 6, and 10 mice in the IFN-γ treated group survived as compared to only 2 mice in the control group.

In the second experiment, significantly more mice in the control group died (35 of 35) than in the IFN-γ group (4 of 26) as set forth in Table I.

TABLE 1

Number of Animals Sacrificed for Quantitative Cultures and Mortality At Each Time Period

| Mortality at Each Time Period | Control Group (n = 35) | IFN-γ Treated Group (n = 26) |
| --- | --- | --- |
| Day 1 | | |
| Sacrificed | 7 | 7 |
| Died | 6 | 1 |
| Day 2 | | |
| Sacrificed | 7 | 7 |
| Died | 4 | 1 |
| Day 3 | | |
| Sacrificed | 6 | 8 |
| Died | 5 | 2 |

Figure 2:
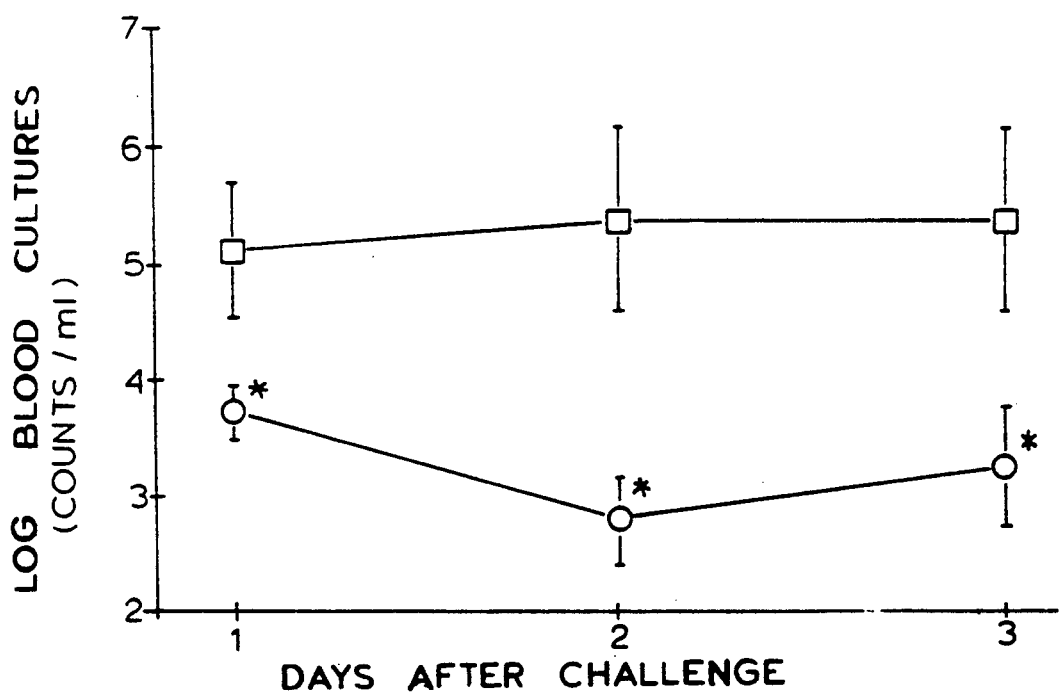
FIG. 2 is a graphic depiction of blood borne bacterial counts for cultures from suture-challenged mice in a control group of suture challenged mice and in a group of mice treated with IFN-$\gamma$ according to the present invention.

The number of animals sacrificed for quantitative bateriology is also shown in Table 1. As illustrated in FIG. 2, the IFN-γ treated group had significantly less systemic blood-borne bacterial counts than the control group for each time period. In FIG. 2, the effect of administration of IFN-γ on blood cultures of mice treated for 5 days prior to suture challenge is plotted using squares to indicate treatment with RPMI-1640 medium (controls) or using circles to indicate treatment with IFN-γ.

There was no difference in local bacterial recovery at the site of infection between the IFN-γ treated group and control group for any time period.

Pretreatment of mice with IFN-γ significantly reduced the mortality observed using the model. This indicates that IFN-γ treatment alters the curse of surgical wound infection.

In the second experiment, recovery of bacteria at the local site of infection was not altered in IFN-γ treated mice; however, recovery of bacteria from the circulation of IFN-γ treated mice was reduced significantly compared to controls. This suggests that the IFN-γ treatment enhances the ability of the host to limit the spread of bacterial infections. The limitation on the spread of bacterial infection may contribute to the decreased mortality observed in mice treated with IFN-γ.

EXAMPLE 2

The efficacy of IFN-γ in prophylaxis and therapy was studied in a simulated wound infection model using a typical surgical pathogen. Groups of 12 CBA/J mice were subcutaneously injected with either murine IFN-γ Or RPMI-1640 medium (controls). The murine IFN-γ was produced by recombinant DNA technology (specific activity $2.3 \times 10^7$ units/mg protein) and was a gift of Genentech, Inc. Bacterial challenge consisted of intramuscular injections of $K.$ Pneumoniae ($10^3$ organisms in 0.1 ml of physiological saline).

Mice pretreated with IFN-γ at a dose of 7,500 or 750 units per day for 3 days, infected, and then treated therapeutically for 2 days survived significantly longer than controls or mice treated with 150 units of IFN-γ per day. Significantly ($p<0.05$) greater survival than controls was observed with pretreatment for 5 or 3 days with IFN-γ, but not with 1 day of pretreatment.

Administration of IFN-γ to the opposite hind limb from the one receiving bacterial challenge was as effective as treatment in the same limb. When IFN-γ treatment was commenced 1 hour after bacterial challenge and continued for 7 days, 13 of 60 mice survived, a significantly ($p<0.05$) greater number than the 4 of 60 surviving controls.

These data confirm that IFN-γ is effective in pretreatment of *Klebsiella pneumoniae* infection of mice. Furthermore, these results support the therapeutic efficacy of IFN-γ in treatment of an extracellular bacterial infection associated with trauma.

EXAMPLE 3

Adult male CBA/J mice, each weighing 20–25 g (Jackson Laboratories, Bar Harbor, Maine), were anesthetized and were burned. Immediately after administration of a burn wound, bacteria were topically applied to the burn wound. The mice were anesthetized using 3.75 mg Ketamine=hydrochloride (Bristol Laboratories, Syracuse, N.Y.) and 0.5 mg Xylazine= (Miles Laboratories, Shaunee, Kansas) in 0.1 ml of physiological saline injected intramuscularly into the right hind limb. The dorsum was clipped with an animal clipper.

The animals were then placed in a mold which was specially designed to expose a predetermined amount of the dorsum while protecting the remainder of the mouse from thermal injury. The mold consisted of a plastic cylinder lined with styrofoam with a large opening on one side through which the mouse was inserted and a smaller opening on the opposite side which exposed an area of the clipped dorsum equal to 30% of the total body surface of the mouse. Full thickness burns were consistently produced by immersion of the exposed dorsum in an 85° C. water bath for 8 seconds. The mice were resuscitated with 2 cc of Ringers lactate administered intraperitoneally.

Two different bacterial challenges were used: $K.$ *pneumoniae* (capsular type 2) and *P. aeruginosa*. Immediately after resuscitation, bacteria ($10^8$ organisms) were administered topically to the burn wound in 1 ml of 10% gelatin using a sterile swab.

Murine IFN-γ was administered subcutaneously into the left hind limb in daily doses of 7500 units in 0.1 ml injections.

The murine IFN-γ, as described in Example 1, was diluted with RPMI-1640 medium. Treatment commenced 5 days prior to burn and bacterial challenge, and the last dose was administered prior to this challenge. In all experiments, control animals received 0.1 ml of RPMI-1640 medium subcutaneously at the same time that the IFN-γ was administered to the experimental animals.

Chi Square tests with Yates correction were used to determine the significance of differences in values obtained in the survival experiments set forth below. The Student's t Test was used to compare groups in experiments involving the expression of Ia antigens on mononuclear cells. In all cases, differences were considered significant at $p<0.05$.

Four experiments were performed. The purpose of the first experiment was to assess the effect of thermal injury alone on survival. Twelve untreated mice were burned and given no bacterial challenge.

Burning without bacterial challenge produced no mortality. All twelve mice survived for three weeks following burning.

The second experiment assessed the effect of IFN-γ on survival of mice with $K.$ *pneumoniae* burn wound infection. Survival of an IFN-γ group (n=47) was compared to a control group (n=48).

Figure 3:
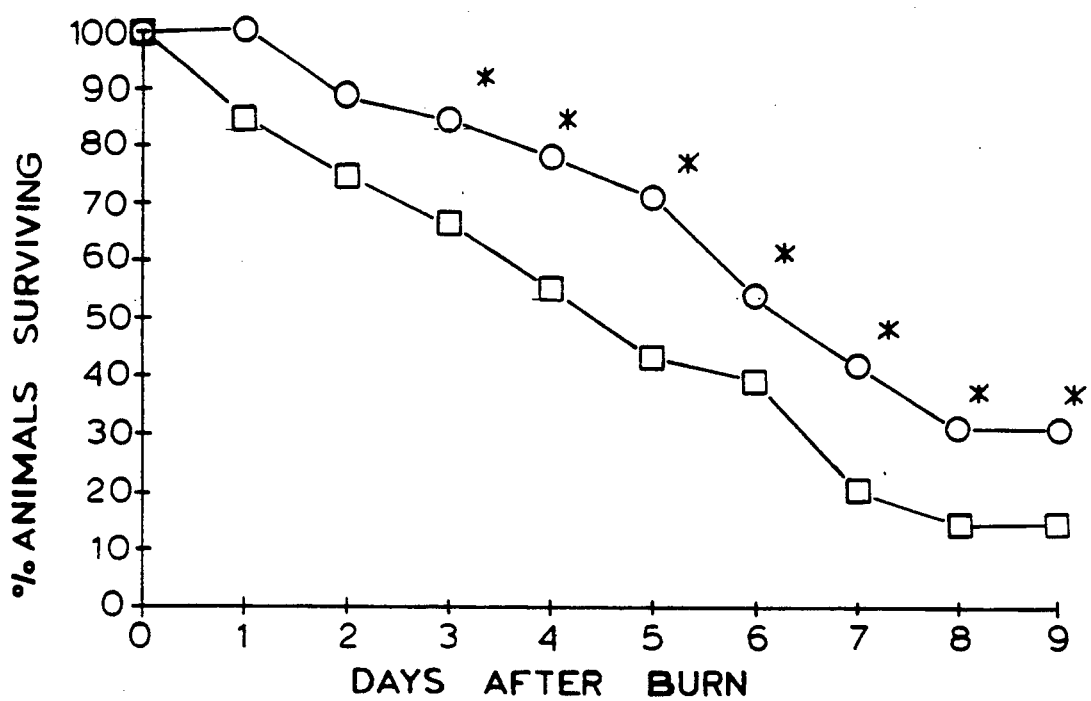
FIG. 3 is a graphic depiction of the effect of IFN-$\gamma$ treatment according to the present invention on survival of mice with a Klebsiella burn wound infection.

When mice had $K.$ *pneumoniae* burn wound infection, there was significantly greater survival in the IFN-γ treated group than the control group from day 3 onwards, as illustrated in FIG. 3 in which a square denotes a value for the control group, a circle denotes a value for the experimental group and an asterisk denotes a value significantly different from the value for the control group on the indicated day. There were no deaths after day 8 of the experiment. Fifteen of 47 mice survived in the group treated with IFN-γ survived compared to 7 of 48 surviving mice in the control group.

Figure 4:
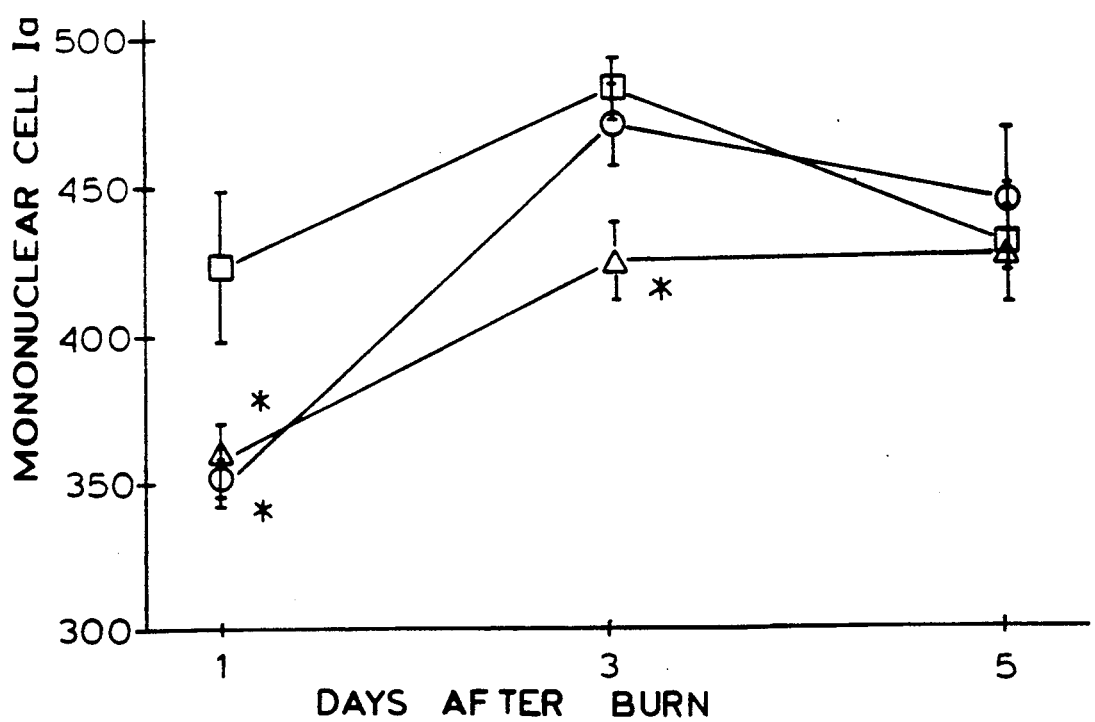
FIG. 4 is a graphic depiction of the effect of burn and an IFN-$\gamma$ treatment according to the present invention on the expression of Ia antigen on peripheral mononuclear cells of mice.

Burn alone significantly decreased mononuclear cell Ia antigen expression compared to controls on days 1 and 3, as illustrated in FIG. 4. In FIG. 4, square denotes a value for the control group, a triangle denotes a value for the burned but untreated group, a circle denotes a value for the experimental (burn plus IFN-γ) group, an asterisk denotes a value significantly different from the value for the control group on the indicated day, and the error bars indicate the standard error of the mean.

The Ia antigen expression returned to normal by day 5 post-burn. Treatment of burned mice with IFN-γ prevented the drop in mononuclear cell Ia antigen expression on day 3 post-burn. In animals which were not burned, there was no difference between the control group and the group receiving IFN-γ alone (not shown) at any time.

The third experiment assessed the effect of IFN-γ on survival of mice with *P. aeruginosa* burn wound infection. Survival in an IFN-γ group (n=27) was compared to survival in a control group (n=28).

When mice had *P. aeruginosa* burn wound infection there was no difference observed in survival between the IFN-γ treated group and the control group.

In the foregoing three experiments, surviving mice were followed for a minimum of 3 weeks after bacterial challenge to assess late mortality.

The fourth experiment assessed the effect of burn and IFN-γ treatment on peripheral mononuclear cell Ia antigen expression. One hundred and forty one mice were divided into four groups. One group received only a burn (n=39), one group received a burn and IFN-γ(n=39), and a control group (n=39) received no treatment. The final group received only IFN-γ(n=24). Thirteen animals in each of the first three groups and 8 from the IFN-γ alone group were sacrificed on days 1, 3 and 5 post burn. Blood was obtained by cardiac puncture and mononuclear cells were assayed for levels of Ia antigen expression.

Aliquots (100μl) of heparinized blood from each mouse were stained for 20 minutes with a fluorescein isothiocyanate-conjugated monoclonal anti-Ia antibody (MA3 043, clone OX6, Accurate Chemical and Scientific Corp., Westbury, N.Y.). Erythrocytes were lysed with 1 ml of lysing reagent (Ortho Diagnostics, Raritan, N.J.). The specimens were then washed in buffer and fixed in 1% paraformaldehyde in phosphate buffered saline (pH 7.4) prior to flow cytometric analyses. Stained samples were analyzed on an Ortho Cytofluorograph IIs flow cytometer (Ortho Diagnostics, Westwood, Mass.). Two thousand mononuclear cells were selected for fluorescent analysis by forward versus right angle light scattering properties.

The percentage of cells staining for Ia antigen was recorded for each specimen. Complete white blood cell counts (obtained using a Coulter Counter, Coulter Electronics, Inc., Edison, N.J.) and Wright-stained microscope differential counts were made, and the absolute number of mononuclear cells was determined. The total Ia antigen expression per sample was calculated by multiplying the number of mononuclear cells by the value for the percent of cells staining positively for Ia antigen.

When mice were treated for five days with IFN-γ prior to burn wound and bacterial challenge, survival was enhanced significantly in $K.$ $pneumoniae$-infected mice compared to controls. No significant changes in survival were noted in mice which were pretreated with IFN-γ, prior to a burn wound, for infection with $P.$ $aeruginosa$. Different bacteria may respond to varying degrees to this treatment protocol in this burn wound infection model.

Different protocols of IFN-γ treatment, perhaps combined with antibiotic chemotherapy, may be useful for successful therapy of $P.$ $aeruginosa$ infections. For example, in preliminary experiments, the addition of 2-5 days of daily subcutaneous injection of 7500 units of IFN-γ into the left hind limb $after$ burn and bacterial challenge appeared to increase resistance of burned mice to some strains of $P.$ $aeruginosa.$ Optimization of treatment protocols or of dosage of IFN-γ, Or the combination of IFN-γ with other materials may contribute to further improved results.

Because of its immunoregulatory properties, IFN-γ, may play a crucial role in modulating host defenses against infection of burns. In the above experiments, decreased Ia antigen expression on mononuclear cells was observed in burned mice. Maintenance of Ia antigen expression in burned mice treated with IFN-γ may contribute to the enhanced resistance of mice to infection with $K.$ $pneumoniae.$

EXAMPLE 4

Adult male CBA/J mice (H-2$^k$) [Jackson Laboratories, Bar Harbor, Maine] weighing 20 to 25 g each were lightly anesthetized using ether and placed in a supine position. An approximately 2.5 cm midline abdominal incision was made, and care was taken to avoid injury to the abdominal contents. The abdominal cavity was lavaged with 3 ml of lactated Ringer's solution (Abbott Laboratories, Chicago, Ill.) and then closed using 4-0 nylon sutures. Next, the skin was closed with silk sutures, and normal saline (0.5 ml) was administered subcutaneously. Animals were then returned to their cages and were allowed food and water ad libitum. Mice that had undergone laparotomy ate and drank normally and did not show any signs of illness. Laparotomy without bacterial challenge produced no mortality.

$E.$ $coli$ ($10^5$ organisms) were administered in 1 ml intraperitoneal injections one-half hour prior to laparotomy. $K.$ $pneumoniae$ (capsular type 2) was administered in 0.1 ml intramuscular injections into the right hind limb on day 5 following laparotomy, unless otherwise indicated.

Murine IFN-γ, as described in Example 1, was diluted with RPMI-1640 medium (GIBCO Laboratories, Grand Island, N.Y.). IFN-γ was administered in daily, tuboulaneous 0.1 ml injections of 7,500 units each. Therapy commenced 1 hour after laparotomy and the last dose was administered 1 hour prior to the second bacterial challenge. In all experiments, control animals received 0.1 ml of RPMI-1640 medium subcutaneously.

A first experiment was directed at determination of an inoculum of $E.$ $coli$ that would cause an LD$_{20}$ when injected intraperitoneally prior to laparotomy. Twenty-seven mice were divided into three equal groups. The groups received inocula of $10^3$, $10^5$, or $10^8$ organisms/ml and were observed for survival.

Two further experiments assessed the effect of IFN-γ on survival in a dual bacterial challenge model. The first of the two experiments compared an IFN-γ-treated group with a control group (n=39 for both groups). Bacterial challenges were $10^5$ $E.$ $coli$ followed by $10^3$ K. pneumoniae five days later. The second of the two experiments assessed the effect of reduction of IFN-γ therapy to 3 days (n=32 in both groups). Bacterial challenge was the same as in the previous experiment, except $K.$ $pneumoniae$ was administered 3 days after $E.$ $coli.$ An additional six experiments were carried out to determine whether IFN-γ used in combination with clinically relevant antibiotics in the laparotomy model caused any toxic effects. The antibiotic regimen and bacterial challenges used in each experiment are summarized in Table 2. In each experiment, animals were divided equally into an IFN-γ treated group and a control group.

TABLE 2

| Antibiotics Used | Number of Animals in Each Group | E. coli (Organisms/ml) | Klebsiella (Organisms/ml) | Survivors in Each Group IFN-γ | Control |
|---|---|---|---|---|---|
| Cefazolin (1 mg/kg) + Tobramycin (1 mg/kg) | 24 | $10^5$ | $10^4$ | 23 | 23 |
| Cefazolin (1 mg/kg) + Tobramycin (1 mg/kg) | 30 | $10^8$ | $10^5$ | 4 | 3 |
| Cefazolin (1 mg/kg) + Tobramycin (1 mg/kg) | 28 | $10^7$ | $10^5$ | 24 | 25 |
| Cefazolin (1 mg/kg) + Tobramycin (1 mg/kg) | 25 | $10^8$ | $10^4$ | 6 | 6 |
| Sulfamethoxazole (50 mg/kg) + Trimethoprim (10 mg/kg) | 33 | $10^8$ | $10^5$ | 27 | 26 |

TABLE 2-continued

| Antibiotics Used | Number of Animals in Each Group | E. coli (Organisms/ml) | Klebsiella (Organisms/ml) | Survivors in Each Group | |
|---|---|---|---|---|---|
| | | | | IFN-γ | Control |
| Sulfamethoxazole (25 mg/kg) + Trimethoprim (5 mg/kg) | 33 | $10^8$ | $10^5$ | 25 | 23 |

In all of the above experiments, surviving mice were observed for a minimum of 3 weeks to assess any possible late mortality.

Another experiment assessed the effect of laparotomy and IFN-γ on peripheral mononuclear Ia antigen expression. Two hundred and forty mice were divided into 4 equal groups. One group received only a laparotomy, one received a laparotomy and IFN-γ, one received only IFN-γ, and one received no treatment. Fifteen animals in each group were sacrificed on days 1, 3, 5 and 7 post-laparotomy (or following IFN-γ treatment in the control group). Blood was obtained by cardiac puncture and mononuclear cells assayed for levels of Ia antigen expression.

Two different antibiotic regimens were used. In the first, cefazolin and tobramycin (Eli Lilly and Co., Indianapolis, Ind.) were used. Both drugs were administered in 0.1 ml intramuscular injections in the left hind limb at dosages of 1 mg/kg body weight. Cefazolin was administered 15 minutes after the first bacterial challenge, but prior to laparotomy. Cefazolin and tobramycin were then administered together daily commencing 1 hour after laparotomy and continuing for 5 days until the second bacterial challenge. Tobramycin was then administered alone daily for 3 days commencing 1 hour after the second bacterial challenge.

In the second antibiotic treatment regimen, Bactrim TM (Roche Laboratories, Nutley, N.J.), a combination product of trimethoprim (16 mg/ml) and sulfamethoxazole (80 mg/ml), was administered, after appropriate dilution, in 0.1 ml intramuscular injections in the left hind limb. The first injection was administered 15 minutes after first bacterial challenge. Bactrim TM was next administered 1 hour after laparotomy and daily thereafter until 3 days after the second bacterial challenge. Two experiments were performed using this regimen, a high dose experiment (10 mg/kg body weight trimethoprim) and a low dose experiment (5 mg/kg body weight trimethoprim).

One hundred microliter aliquots of heparinized blood from each mouse were stained for 20 minutes with fluorescein-isothiocyanate-conjugated monoclonal anti-Ia (MAS 043p, clone 0X6, Accurate Chemical and Scientific Corp., Westbury, N.Y.). Erythrocytes were lysed with 1 ml of lysing reagent (Ortho Diagnostics, Raritan, N.J.). The specimens were then washed in buffer and fixed in 1% paraformaldehyde in phosphate buffered saline (pH 7.4) prior to flow cytometric analyses.

Stained samples were analyzed on an Ortho Cytofluorograph IIs flow cytometer (Ortho Diagnostics, Westwood, Mass.). Two thousand mononuclear cells were selected for fluorescent analysis by forward versus right angle light scattering properties. A percent of cells staining for Ia antigen was recorded for each specimen. Complete white blood cell counts (Coulter Counter, Coulter Electronics, Inc., Edison, N.J.) and Wright-stained microscope differential counts were made, and an absolute number of mononuclear cells was determined. The total Ia antigen expression per sample was calculated by multiplying the number of mononuclear cells by the value for the percent of cells staining positively for Ia antigen.

Chi Square tests were used to determine differences in the survival experiments. The Student's t Test was used to compare groups in the experiments involving the expression of Ia antigens on mononuclear cells. In all cases, differences were considered significant at $p < 0.05$.

Figure 5:
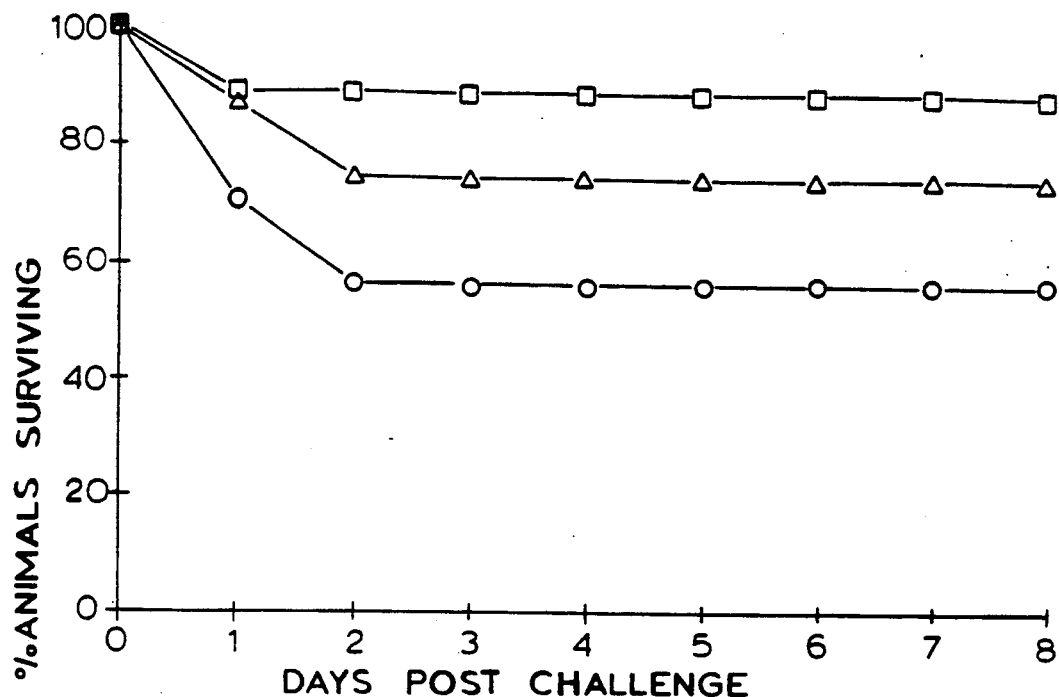
FIG. 5 is a graphic depiction of the survival of mice following peritoneal inoculation of different concentrations of E. coli prior to laparotomy.

Mice infected with E. coli were assessed for survival 2 days after initial infection. Results are shown in FIG. 5. In FIG. 5, a square denotes values for the group which received $10^3$ organisms/ml, a triangle denotes values for the group inoculated with $10^5$ organisms/ml, and a circle denotes values for the group which received $10^8$ organisms/ml. No additional deaths occurred after that time. The dosage of $10^5$ organisms/ml of E. coli was chosen as the first bacterial challenge for all additional experiments because this dose yielded the closest dose to an $LD_{20}$.

When mice received 5 days of therapy with IFN-γ, there was greater survival in the IFN-γ treated group than in the control group, as illustrated in FIG. 6. In FIG. 6, a square denotes values for the control group, a circle denotes values for the IFN-γ-treated group, and an asterisk indicates a statistically significant difference between the values for the IFN-γ treated group and the control group on the date shown. When mice received only 3 days of therapy with IFN-γ, there was also greater survival in the group treated with IFN-γ than in the control group, as illustrated in FIG. 7. In FIG. 7, a square denotes values for the control group, a circle denotes values for the IFN-γ-treated group, and an asterisk indicates a significant difference between the values for the IFN-γ-treated group and the control group on the indicated day.

The number of mice surviving after day 15 is shown in Table 2. There were no further deaths after that time in any group. There were no significant differences in survival between IFN-γ treated and IFN-γ antibiotic-treated groups, as set forth in Table 2. This indicated no toxic effect of the dual modality therapy. However, this model was not designed to demonstrate a synergistic effect between IFN-γ and antibiotics.

Figure 8:
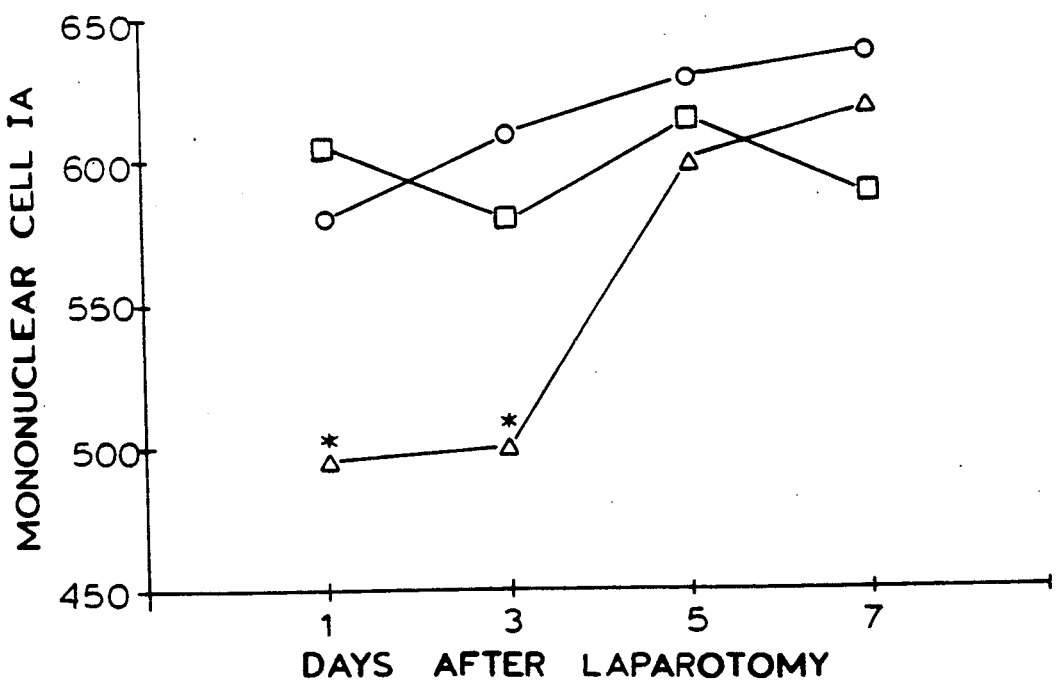
FIG. 8 is a graphic depiction of the effect of laparotomy IFN-$\gamma$ treatment on the expression of Ia antigen on peripheral mononuclear cells.

Laparotomy alone significantly decreased mononuclear cell Ia antigen expression compared to controls on days 1 and 3 post-surgery, as illustrated in FIG. 8. In FIG. 8, values for the control group are denoted by a square, values for the laparotomy alone group by a triangle, values for the laparotomy and IFN-γ treatment group by a circle, while an asterisk indicates a statistically significant difference. The Ia antigen expression returned to normal by day 5 post-surgery. Treatment of laparotomized mice with IFN-γ prevented the drop in mononuclear cell Ia antigen expression on days 1 and 3 post-surgery.

EXAMPLE 5

Eleven consecutive patients who sustained major trauma resulting in an Injury Severity Score ("ISS") [Baker et al., J. Trauma, 14, 187–196 (1984)] of at least 20 were studied. These patients sustained the following injuries: burns (5 patients), gunshot wounds (3 patients), motor vehicle accidents (2 patients), and crush injury (1 patient). Blood samples were obtained within 5 days of injury. Ten healthy normal subjects were also studied.

Three series of experiments were performed. The first assessed the effect of trauma on monocyte HLA-DR expression. An experiment assessed the effect of IFN-$\gamma$ on monocyte HLA-DR antigen expression in mononuclear cell culture in trauma patients (n=11) and normal subjects (n=10). Four patients had serial tests performed throughout their hospital stay. The final experiment assessed the effect of IFN-$\gamma$ on monocyte HLA-DR antigen expression in pure monocyte culture for trauma patients (n=5) and normal subjects (n=4).

Human affinity-purified IFN-Y (Interferon Sciences, Inc., New Brunswick, N.J.) was used. The IFN-$\gamma$ had a specific activity of approximately $1.0 \times 10^6$ units/mg protein and was diluted with sterile phosphate-buffered saline. IFN-$\gamma$ (500 units) were added to each culture. In all experiments, controls were set up with culture media alone added.

Mononuclear cells were isolated and cultured as follows. Twenty milliliters of venous blood were collected in acid citrate dextrose anticoagulate tubes (Becton-Dickinson, Rutherford, N.J.). Mononuclear cells were separated from whole blood diluted 1:4 with RPMI-1640 medium (Gibco Laboratories, Grand Island, N.Y.) by centrifugation for 30 minutes at 1500 rpm after layering on Ficoll hypaque-1077 TM gradients. (Sigma Chemical Co., St. Louis, Miss.) at a 4:3 ratio. The mononuclear layer was harvested, washed twice with RPMI-1640 medium and resuspended in RPMI-1640 medium supplemented with 5% human AB serum (Hazelton Laboratories, Hazelton, Pa.), $2 \times 10^{-5}$-mercaptoethanol, 300 units of penicillin, 300 mg of streptomycin and 75 pg of amphotericin B. Mononuclear cell cultures were established with $2 \times 10^6$ cells in 1.5 ml volumes per siliconized glass tube and incubated for 48 hour at 37° C. in 5% $CO_2$.

Monocytes were purified and cultured as follows. Twenty milliliters of venous blood were collected in EDTA anticoagulate tubes (Becton-Dickinson, Rutherford, N.J.). Whole blood was diluted 10:1 with dextran 500, and allowed to stand for 1 hour in room temperature to permit neutrophils to settle. Plasma was extracted, passed over Nycodenz TM (Accurate Chemicals, Westbury, N.Y., and then centrifuged for 20 minutes at 2000 rpm. Purified monocytes were collected and washed with RPMI-1640 medium. These purified monocytes were then resuspended and cultures were established as previously described.

The expression of HLA-DR antigen on monocytes was determined using dual monoclonal antibody staining and flow cytometry. One million cells of each preparation were stained with anti-human fluorescein coupled $MO_2$ monoclonal antibody (Coulter Immunology, Hialeah, Fla.), which specifically stains monocytes, and with isothiocyanate-coupled anti-human HLA-DR antigen (Becton-Dickinson, Sunnyvale, Calif.). Samples were analyzed on an Orthocytofluorograph IIs flow cytometer (Ortho Diagnostics, Westwood, Mass.) configured for simultaneous 2-color (red and green) fluorescent analysis. Gain settings were set on stained calf thymus standards (Fluortrol TM, Ortho Instruments, Westwood, Mass.). In this analysis, HLA-DR antigen expression was measured only on cells which co-stained positively for $MO_2$ antigen, thereby excluding all cell types other than monocytes from the analysis.

In all experiments, two parameters were measured, the percentage of monocytes which expressed HLA-DR antigen and the density of the HLA-DR antigen expression on monocytes. The density of HLA-DR antigen expression on monocytes was measured as the mean fluorescent channel on gated positive cells (1000 channel resolution).

The Student's t Test was used to determine differences. Differences were considered significant at $p < 0.05$.

The mean HLA-DR antigen density on monocytes of trauma patients was $85.8 \pm 15.5$ for normal subjects. The mean value for percentage of monocytes expressing HLA-DR antigen of trauma patients was $31.6\% \pm 6.5$ and was significantly less than the mean of $91.1\% \pm 2.5$ for normal subjects.

Figure 9:
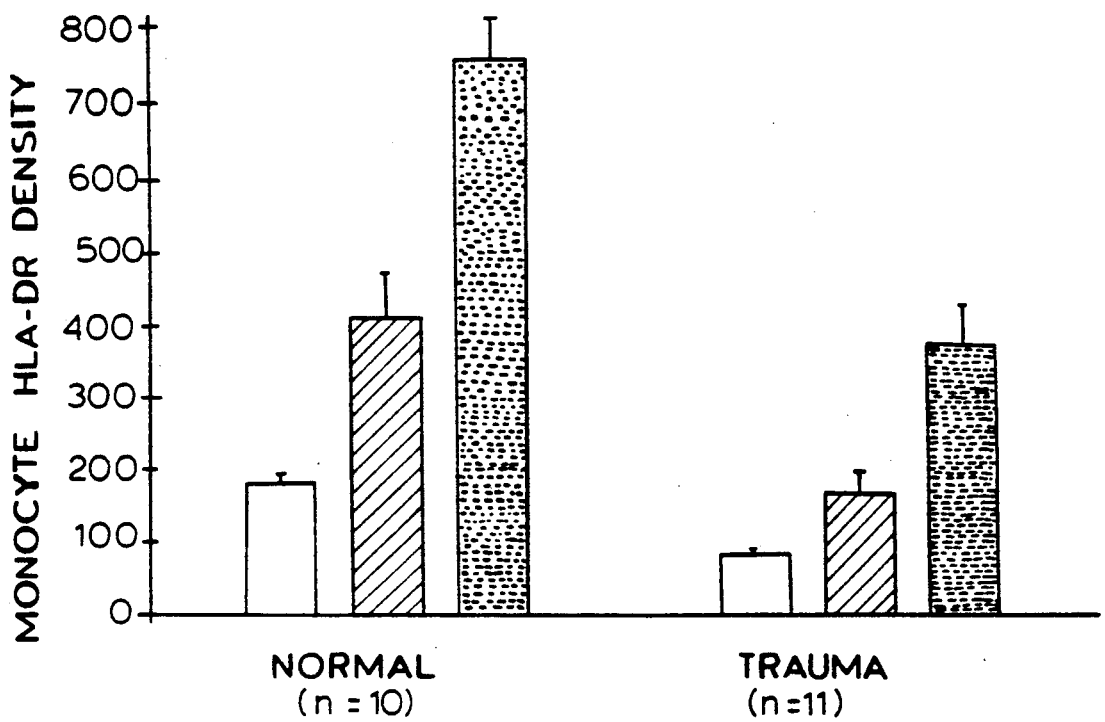
FIG. 9 is a graphic depiction of the effect of IFN-$\gamma$ treatment of peripheral blood mononuclear cell cultures with respect to the density of monocyte HLA-DR expression of trauma patients.

Mixed lymphocyte and monocyte culture alone, without IFN-$\gamma$ addition, increased the density of HLA-DR antigen expression on monocytes in both normal subjects and trauma patients. IFN-$\gamma$ treatment significantly increased the density of monocyte HLA-DR antigen expression above culture alone values in both normal subjects and trauma patients, although the levels for trauma patients treated with IFN-$\gamma$ were less than the normal level, as illustrated in FIG. 9. In FIG. 9, an empty bar represents a baseline value, a hatched bar represents a value for 48 hour culture, a solid bar represents a value for 48 hour cultures with IFN-$\gamma$, and an error bar indicates the standard error of the mean for each value.

Figure 10:
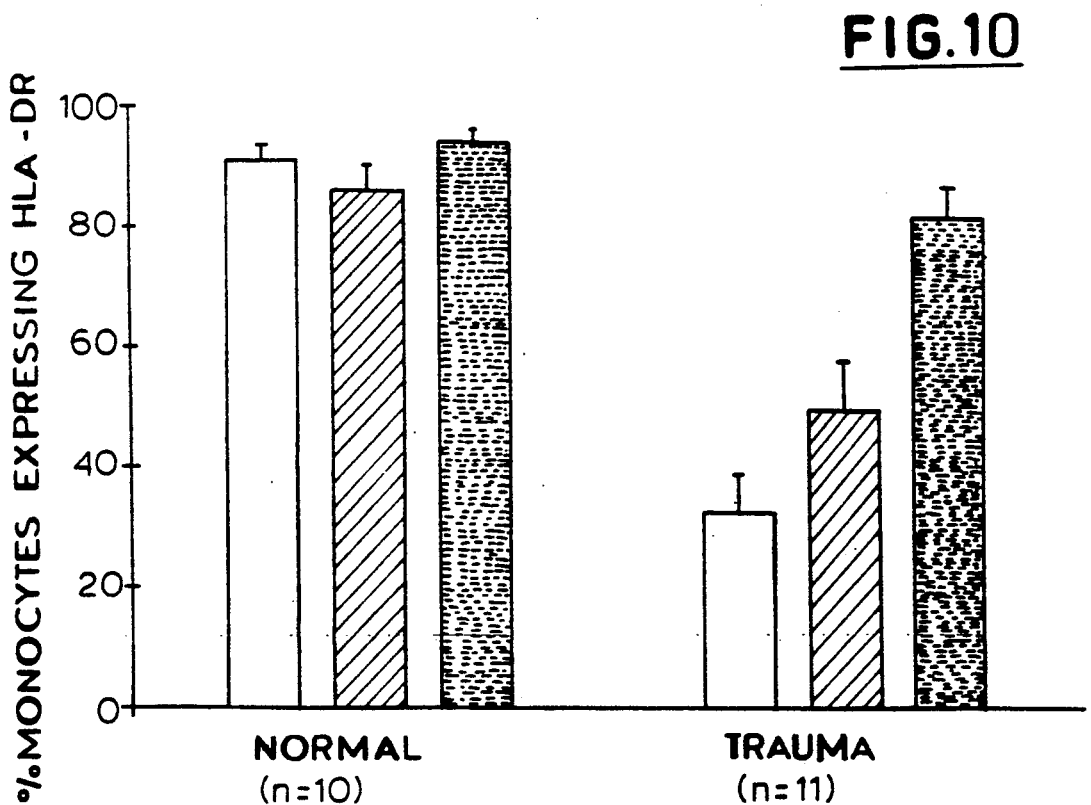
FIG. 10 is a graphic depiction of the effect of IFN-$\gamma$ treatment on peripheral blood mononuclear cell cultures with respect to the percentage of monocytes expressing HLA-DR antigen.

IFN-$\gamma$ treatment significantly increased the percentage of monocytes expressing HLA-DR antigen above culture alone and baseline values, as illustrated in FIG. 10. In FIG. 10, an empty bar represents a baseline value, a hatched bar represents a value for 48 hour culture, a solid bar represents a value for 48 hour culture with IFN-$\gamma$, and an error bar indicates the standard error of the mean for each value. This value was not different from the baseline value for normal subjects and approached the IFN-$\gamma$ value for normal subjects.

Figure 11:
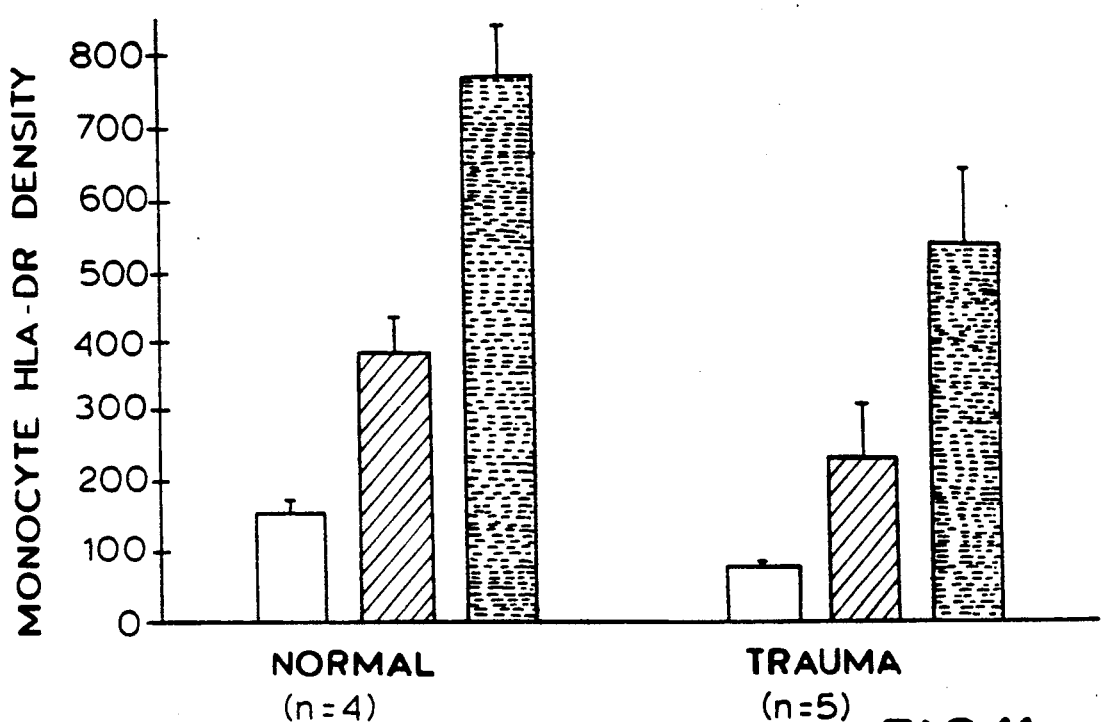
FIG. 11 is a graphic depiction of the effect of IFN-$\gamma$ treatment of purified monocyte cultures on the density of monocyte HLA-DR antigen expression of trauma patients.
Figure 12:
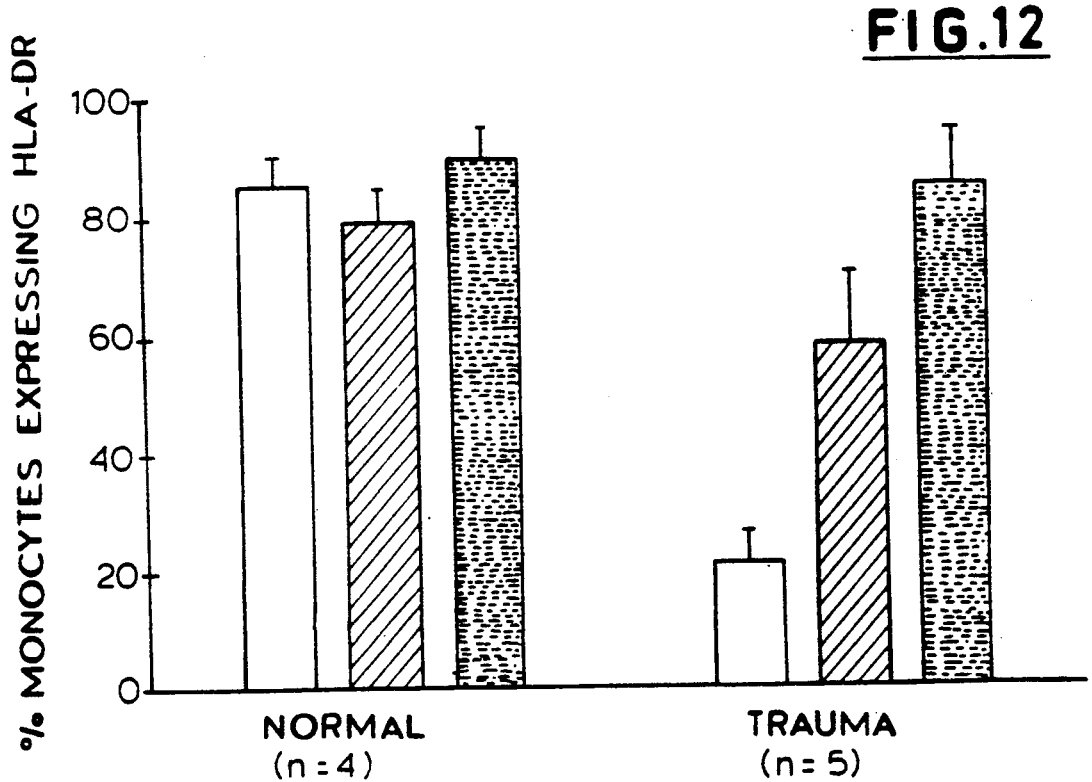
FIG. 12 is a graphic depiction of the effect of IFN-$\gamma$ in purified monocyte cultures on the percentage of monocytes expressing HLA-DR antigen.

In purified monocyte culture, culture alone significantly increased both density of monocyte HLA-DR antigen expression, as depicted in FIG. 11, and increased the percentage of monocytes expressing HLA-DR antigen above baseline values in the trauma group but not in the normal subjects group, as depicted in FIG. 12. In FIGS. 11 and 12 an empty bar represents a baseline values, a hatched bar represents values for 48 hour culture, a solid bar represents a value for 48 hour culture with IFN-$\gamma$, and an error bars indicates the standard error of the mean for each value. IFN-$\gamma$ treatment significantly increased the density of HLA-DR antigen expression in the trauma and normal groups.

When IFN-$\gamma$ treated cultures were considered, there was no difference between the trauma or normal groups in either density of HLA-DR antigen expression on monocytes, as shown in FIG. 11, or in the percentage of monocytes expressing HLA-DR antigen, as shown in FIG. 12.

Of the four serially-followed patients, two made uneventful recoveries, and one developed major sepsis. IFN-$\gamma$ treatment markedly increased monocyte HLA-DR antigen expression at each time. The other patient died of burn wound infection, and IFN-$\gamma$ treatment increased monocyte HLA-DR antigen expression at each time, even for the final sample, which was obtained immediately prior to death.

Figure 13:
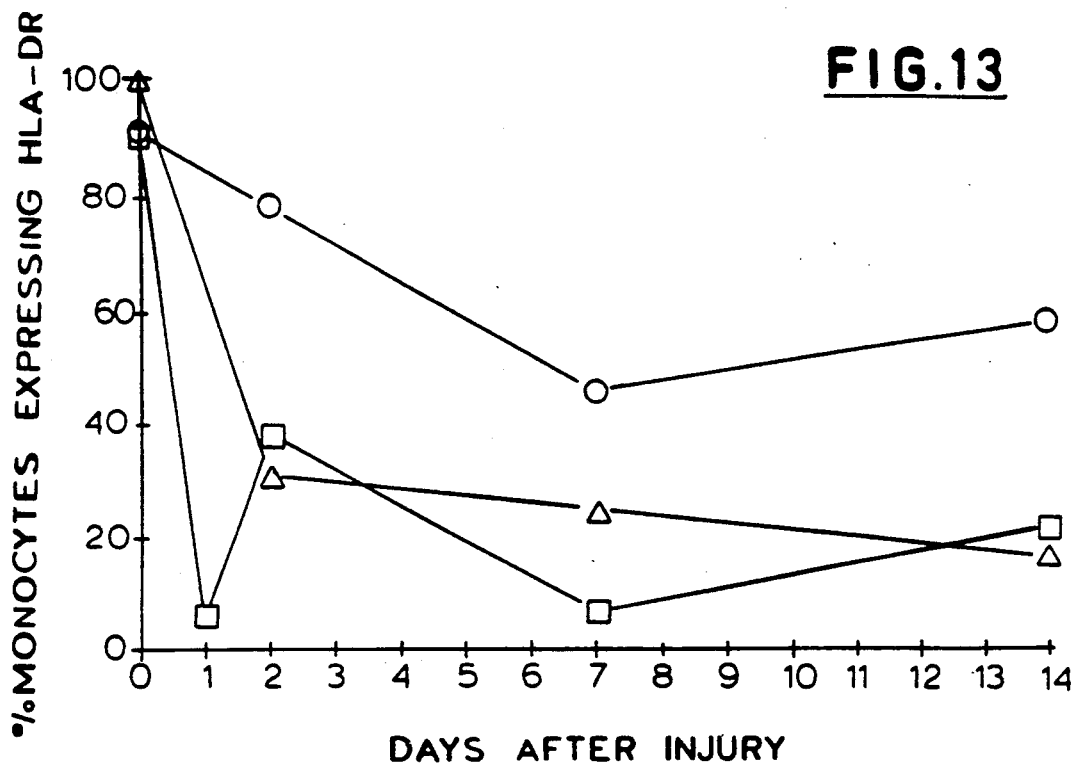
FIG. 13 is a graphic depiction of the effect of IFN-$\gamma$ in peripheral blood mononuclear cell culture on the percentage of monocytes expressing HLA-DR antigen in a patient who died of burn wound sepsis.

FIG. 13 is a graphic depiction of monocyte HLA-DR antigen values for the cultures obtained from the burn patient who died. In FIG. 13, baseline values are denoted by squares, 48 hour culture values by triangles, and 48 hour culture with IFN-γ values by circles.

The results confirm that severely injured patients have depressed levels of HLA-DR antigen expression as compared to controls. When IFN-γ was added to peripheral blood cell cultures obtained from these patients, the IFN-γ treatment resulted in an increase in HLA-DR antigen density of expression on monocytes. This increase in density of HLA-DR antigen expression did not result in a return to the normal range of HLA-DR antigen expression of controls, but there was a positive response to the IFN-γ treatment.

When the percentage of monocytes expressing HLA-DR antigen was considered, a return to a near normal percentage of cells expressing HLA-DR antigen was observed in IFN-γ-treated peripheral blood cell cultures of trauma patients. Similar patterns were observed when cultures of purified monocytes were used, indicating that interaction with lymphocytes in culture may not play a role in this result.

The kinetics of the response to IFN-γ were observed in the culture of the peripheral blood cells of a burn patient who succumbed to a septic infection. From these data, it is clear that HLA-DR antigen expression was depressed on the first day following injury, but that IFN-γ was capable of enhancing the percentage of monocytes expressing HLA-DR antigen until the last day of life for this patient.

The results of this study indicate that HLA-DR antigen expression is depressed on monocytes of trauma patients, but that IFN-γ treatment may at least partially restore HLA-DR antigen expression. The resistance to infection of many trauma patients may be compromised as a result of impaired antigen presentation due to depressed HLA-DR antigen expression. In trauma patients, who are often unresponsive to conventional therapy, IFN-γ may be used to help restore immune defenses.

EXAMPLE 6

In an experiment generally following the procedures of Example 4, blood was collected from 10 normal subjects (control group) and 11 patients who sustained severe trauma (trauma group). A baseline $MO_2DR$ value for each group was determined using dual monoclonal antibody staining and flow cytometry. Polk et al., Ann. Surg., 204, 282-299 (1986). The mononuclear layer of each blood sample was then harvested and incubated with either 500 I.U. IFN-γ (IFN-γ-culture) or control media (culture alone). The $MO_2DR$ value for each sample was determined after 48 hours of incubation.

The mean baseline $MO_2DR$ value for the trauma group was 32%, which was significantly less than the mean $MO_2DR$ value of 91% for the control group ($p<0.001$). In the trauma group, IFN-γ cultured $MO_2DR$ value was 81% which was significantly greater than both the mean baseline $MO_2DR$ value of 32% ($p<0.001$) and the 49% mean value of $MO_2DR$ value when cultured without IFN-γ ($p<0.01$). In the control group, there were no significant differences among the IFN-γ culture $MO_2DR$ value (94%), the culture alone $MO_2DR$ value (86%) or the baseline $MO_2DR$ value (91%). These data confirm that HLA-DR antigen expression on monocytes of severely injured patients is markedly reduced and show that it may be increased significantly by IFN-γ. IFN-γ may be an important augmentor of host defense mechanisms in these patients.

EXAMPLE 7

Patients with severe injury [ISS >20 and 1+or 2+bacterial contamination of their wounds, scored according to the procedure of Hershman et al., *Injury*, 19, 263-266 (1988)] received recombinant human IFN-γ (Genentech, Inc., South San Francisco, Calif.) at doses of 0.01 to 0.1 mg/m²/day for 7-10 days immediately following hospitalization. Standardized prophylactic antibiotic therapy with cefoxitin was administered during the first 72 hours. Patients were monitored for infection and monocyte DR antigen expression, the latter being an immunologic endpoint used as an indicator of clinical outcome.

Treatment at all dose levels was extremely well tolerated. Fever was the only drug-related toxicity observed, and fever was only observed at the two higher doses. Among the first 13 patients treated, there were only two episodes of major sepsis and no deaths related to sepsis. Monocyte DR antigen expression, which is depressed in severe trauma victims, was restored to normal or greater than normal levels. Individual case summaries for five of the patients treated on this study are as follows.

Patient BD was a 20 year old male who had suffered full thickness esophageal burns due to the ingestion of a caustic cleaning substance. His ISS was 25 and he had 1+bacterial contamination in his wound. He received IFN-γ therapy at a dose of 0.01 mg.m/² for seven days and cefoxitin prophylaxis for 72 hours. He recovered fully from this injury without major sepsis.

Patient TR was a 24 year old female who suffered a gunshot wound to the abdomen with injury to the pancreas and inferior vena cava. Her ISS was 25 and she had 1+ bacterial contamination of her wound. She was treated with IFN-γ at a dose of 0.01 mg/m² for seven days and cefoxitin prophylaxis. Nafcillin was also administered. Other than a culture of *Staphylococcus aureus* from her central venous catheter tip, the patient had no evidence of infection and recovered fully from her injury.

Patient MD was a 28 year old male who suffered multiple stab wounds to the head and chest. His ISS was 26 with 1+bacterial contamination of the wound. The patient received recombinant IFN-γ therapy at a dose of 0.01 mg/m² for seven days as well as cefoxitin antibiotic prophylaxis. The patient recovered fully and had no evidence of major sepsis.

Patient BD was a 27 year old female who suffered severe pelvic injury due to a motor vehicle accident. The ISS was 25 with 1+ bacterial contamination of the wound. The patient was treated with IFN-γ at a dose of 0.01 mg/m² for seven days as well as cefoxitin antibiotic prophylaxis. In addition, flagyl and amikacin were administered. The patient recovered fully from her injury without evidence of major sepsis.

Patient BD was a 27 year old male who suffered a gunshot wound to the abdomen. His ISS was 25 with 1+ bacterial contamination. He received recombinant IFN-γ therapy at a dose of 0.1 mg/m² for seven days as well as cefoxitin antibiotic prophylaxis. The patient developed an intra-abdominal abscess which required drainage and further antibiotic therapy, but then recovered fully from this injury.

EXAMPLE 8

Adult female Sprague-Dawley rats (Harlan Sprague-Dawley, Indianapolis, Ind.) weighing 190–230 g were subjected to hemorrhagic shock. The rats were anesthesized with intraperitoneal Ketamine (50 mg/kg) and Xylazine ™ (15 mg/kg) and bled to a mean arterial pressure of 45 mm Hg which was maintained for 45 minutes. Animals were resuscitated with their shed blood and approximately 1.5 volumes normal saline. The mortality of this hemorrhagic shock protocol was approximately 15%; all deaths occurred within 24 hours following shock and these animals were excluded from analysis.

Staphylococcus aureus 502A (ATCC 27172, American Type Culture Collection, Rockville, MA.) was maintained on trypticase soy agar at 4° C. Prior to use, the bacteria were grown overnight in trypticase soy broth at 37° C., washed and resuspended in normal saline at a concentration of $4 \times 10^8$ colony forming units (CFU) per ml. The bacterial concentration was determined by measuring the optical density at 620 nm and confirmed by serial dilution and backplating on trypticase soy agar.

Recombinant rat IFN-γ was purchased from Amgen Biologicals (Torrence, Calif.) and had a specific activity of $4.8 \times 10^6$ U/mg. IFN-γ was diluted with phosphate buffered saline containing 2% rat serum and was stored at $-70°$ C. prior to use.

One hour after resuscitation from hemorrhagic shock, animals were injected with 5 separate inocula of $1 \times 10^8$ CFU (0.25 ml) Staphylococcus aureus ("S. aureus") subcutaneously on the dorsum. Animals were divided into four treatment groups: a first group of control animals were resuscitated following shock but received no further treatment; a second group of antibiotic-treated animals received cefazolin ("CEF") (Smith, Kline and French, Philadelphia, Pa.) intraperitoneally at 30 mg/kg, 30 minutes prior to inoculation and then again 4 hours later; a third group of IFN treatment-animals received IFN-γ 7500 U subcutaneously, one hour following inoculation and then daily for three days; and a fourth group received both CEF and IFN-γ as in groups 2 and 3. Tissue antibiotic levels were measured in the subcutaneous tissue 30 minutes after the initial dose of CEF by a standard bioassay.

Animals were sacrificed on day 7 by cervical dislocation under anesthesia. A dorsal incision was made and the skin reflected. The diameter of each abcess was measured in situ with a micrometer, and abcesses were dissected free from the musculature of the back. Abscesses were then excised from the skin and weighed.

Statistical analysis of abscess number was done using Fisher's Exact Test. Comparisons of abscess diameter and weight were made using a prior analysis of variance followed by a Tukey - Kramer HSD Test. Significance was set a priori at $p < 0.05$.

The results for abscess number, diameter and weight are summarized in Table 3. In Table 3, for values indicated by the "§" symbol, a significant difference from the control at the $p < 0.05$ vs. level was determined, and for values identified by an asterisk, a significant difference from the value for CEF alone was determined at the $p < 0.05$ level.

TABLE 3

| EXPERIMENTAL GROUPS | ABSCESS #(n = 20) | ABSCESS DIAMETER (mm) | ABSCESS WT (mg) |
|---|---|---|---|
| Control | 20 | 13.4 ± 1.9 | 504 ± 125 |
| CEF | 20 | 10.1 ± 1.1 | 191 ± 78 |
| IFN | 20 | 14.6 ± 3.8 | 769 ± 212 |
| CEF + IFN | 14* | 4.8 ± 1.6* | 67 ± 59 |

Figure 14:
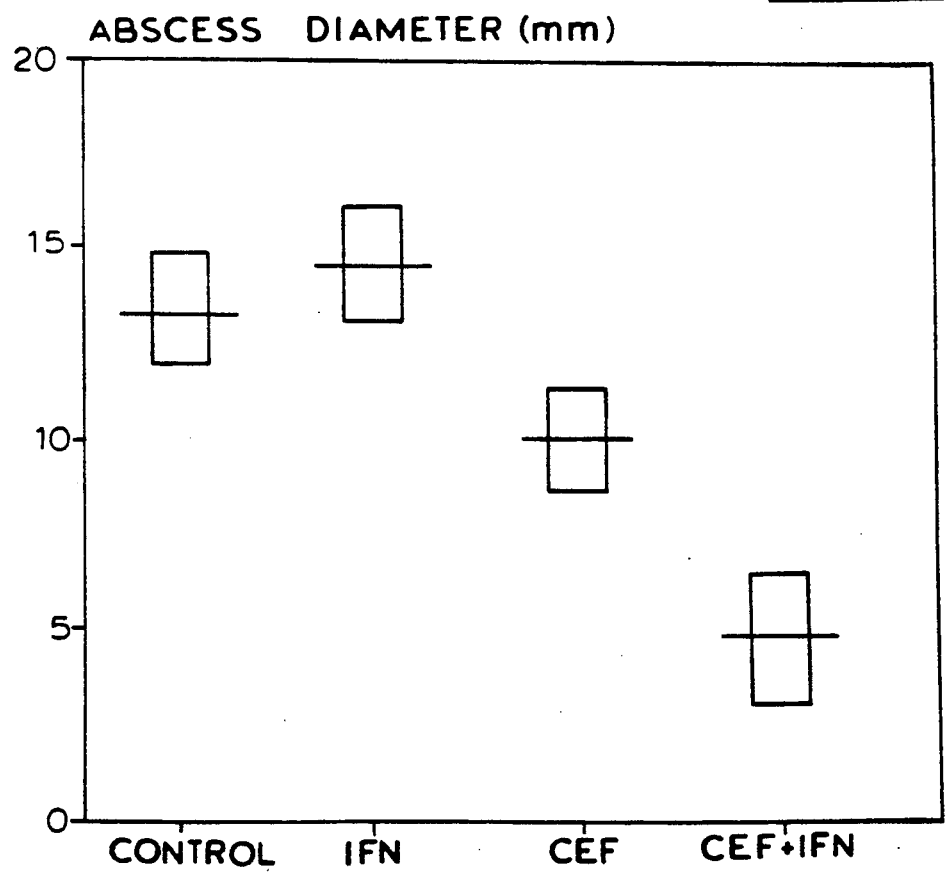
FIG. 14 is a graphic depiction of the synergistic effect on abcess diameter of coadministration of IFN-$\gamma$ and an antibiotic according to the present invention.

The administration of standard antibiotic prophylaxis (CEF) following hemorrhagic shock decreased abscess diameter and weight compared to control but did not decrease abscess number. Animals treated with IFN-γ alone had abcesses which were larger than those of control animals. This correlated with a subjective impression of an increased inflammatory reaction around these lesions. The addition of IFN-γ to CEF significantly decreased abscess number, diameter and weight as compared to the control or to the use of CEF alone. Analysis of the 99% confidence intervals of the mean abscess diameter for each group illustrates the synergy between these immune adjuvants and CEF in decreasing abscess diameter as compared to controls or, as illustrated in FIG. 14, as compared to either modality alone.

Tissue CEF levels were $14.9 \pm 5.2$ μg/gm 30 minutes after the initial dose, exceeding the minimal inhibitory concentration employed for the S. aureus (0.15 μg/ml).

Although the present invention has been described in terms of particular embodiments, it is understood that modifications and variations will occur to those skilled in the art. For example, when IFN-γ is administered via the intravenous route, antibiotics and IFN-γ may be co-administered. Therapy according to the present invention could be used for all types of trauma, and may be used for emergency or elective surgery. Classes of antibiotics useful according to the present invention include, but are not limited to, cephalosporins, penicillins (including semi-synthetic penicillins), bacteriostatic antibiotics and aminoglycosides.

Accordingly, it is intended that the present invention include all variations and modification which come within the scope of the claims.

We claim:

1. A method for the prophylaxis or treatment of trauma-associated sepsis comprising the steps of:
   identifying a subject as having been exposed to trauma or about to be exposed to trauma; and
   administering a plurality of applications of a therapeutically effective dose comprising 750 units of IFN-γ to the patient.

2. A method as recited in claim 1 wherein the patient is not known to have a viral infection, a tumor, or an intracellular infection.

3. The method as recited in claim 1 wherein said administering step comprises the step of subcutaneously injecting a therapeutically effective dose of IFN-γ.

4. The method as recited in claim 1 wherein the sepsis is a bacterial blood infection.

5. The method as recited in claim 1 wherein said administering step comprises the step of intramuscularly injecting a therapeutically effective dose of IFN-γ.

6. The method as recited in claim 1 wherein the trauma is an injury or a surgical incision.

7. The method as recited in claim 1 wherein said administering step comprises the step of intravenously injecting a therapeutically effective dose of IFN-γ.

8. The method as recited in claim 4 wherein the sepsis is caused by an enteric bacterium.

9. The method as recited in claim 1 wherein said administering step comprises the step of introducing a therapeutically effective dose of IFN-$\gamma$ into a bodily fluid of the patient.

10. The method as recited in claim 1 wherein the IFN-$\gamma$ is desCysTyrCys human IFN-$\gamma$.

11. The method as recited in claim 1 further comprising the step of co-administering a therapeutically effective dose of an antibiotic.

12. The method as recited in claim 11 wherein said co-administering step comprises the step of intravenously infusing a composition comprising a therapeutically effective dose of IFN-$\gamma$ and an antibiotic.

13. The method as recited in claim 11 wherein the antibiotic is an antibacterial agent.

14. The method as recited in claim 11 wherein the antibiotic composition is selected from the group consisting of cefazolin, nafcillin, vancomycin, cefoxitin, neomycin plus erythromycin, penicillin G, trimethoprim plus sulfamethoxazole, and clindamycin or clindamycin plus gentamycin or tobramycin.

15. A composition for the prophylaxis or treatment of trauma-associated sepsis comprising:
   a therapeutically effective dose comprising 750 units of IFN-$_{65}$ essentially free from interferons other than IFN-$\gamma$;
   a therapeutically effective dose of an antibiotic; and
   a diluent or carrier.

16. The composition as recited in claim 15 wherein the antibiotic is selected from the group consisting of cefazolin, nafcillin, vancomycin, cefoxitin, neomycin plus erythromycin, penicillin G, trimethoprim plus sulfamethoxazole, and clindamycin or clindamycin plus gentamycin or tobramycin.

17. The composition as recited in claim 15 wherein the antibiotic is an antibacterial agent.

* * * * *